(12) United States Patent
Dekker

(10) Patent No.: US 6,896,661 B2
(45) Date of Patent: May 24, 2005

(54) MONITORING PHYSIOLOGICAL PARAMETERS BASED ON VARIATIONS IN A PHOTOPLETHYSMOGRAPHIC BASELINE SIGNAL

(75) Inventor: Andreas Lubbertus Aloysius Johannes Dekker, Maastricht (NL)

(73) Assignee: Datex-Ohmeda, Inc., Madison, WI (US)

(*) Notice: Subject to any disclaimer, the term of this patent is extended or adjusted under 35 U.S.C. 154(b) by 18 days.

(21) Appl. No.: 10/081,165

(22) Filed: Feb. 22, 2002

(65) Prior Publication Data

US 2003/0163050 A1 Aug. 28, 2003

(51) Int. Cl.⁷ .................................................. A61B 5/08
(52) U.S. Cl. ...................... 600/529; 600/300; 600/481; 600/507
(58) Field of Search ................................. 600/300, 301, 600/481, 500–507, 529–543

(56) References Cited

U.S. PATENT DOCUMENTS

| | | |
|---|---|---|
| 3,704,706 A | 12/1972 | Herczfeld et al. |
| 4,306,567 A | 12/1981 | Krasner |
| 4,379,460 A | 4/1983 | Judell |
| 4,404,974 A | 9/1983 | Titus |
| 4,510,944 A | 4/1985 | Porges |
| 4,765,340 A | 8/1988 | Sakai et al. |
| 4,777,960 A | 10/1988 | Berger et al. |
| 4,781,201 A | 11/1988 | Wright et al. |
| 4,813,427 A | 3/1989 | Schlaefke et al. ......... 128/671 |
| 4,858,638 A | 8/1989 | Cseri ........................ 137/115 |
| 4,860,759 A | 8/1989 | Kahn et al. |
| 4,863,265 A | 9/1989 | Flower et al. ............... 356/41 |
| 4,869,254 A | 9/1989 | Stone et al. |
| 4,884,578 A | 12/1989 | Morgenstern |
| 4,899,760 A | 2/1990 | Jaeb et al. |
| 4,930,517 A | 6/1990 | Cohen et al. |
| 4,958,638 A | 9/1990 | Sharpe et al. |
| 4,960,129 A | 10/1990 | DePaola et al. |
| 4,972,842 A | 11/1990 | Korten et al. |
| 5,033,472 A | 7/1991 | Sato et al. |
| 5,078,136 A | 1/1992 | Stone et al. |
| 5,111,817 A | 5/1992 | Clark et al. |
| 5,170,794 A | 12/1992 | Reiche |
| 5,273,036 A | * 12/1993 | Kronberg et al. ........... 600/310 |
| 5,368,224 A | 11/1994 | Richardson et al. |
| 5,385,144 A | 1/1995 | Yamanishi et al. |
| 5,396,893 A | * 3/1995 | Oberg et al. ................ 600/484 |
| 5,423,322 A | 6/1995 | Clark et al. |

(Continued)

OTHER PUBLICATIONS

Spectral Analysis: Review "Heart Rate Variability", Lukas Spieker, hemodynamics.ucdavis.edu, Unknown Publication Date.

Primary Examiner—Mary Beth Jones
Assistant Examiner—Patricia Mallari
(74) Attorney, Agent, or Firm—Marsh Fischmann & Breyfogle LLP

(57) ABSTRACT

A method and apparatus are disclosed for using photoplethysmography to obtain physiological parameter information related to respiration or the autonomic nervous system. In one implementation, the process involves obtaining (602) a pleth, filtering (604) the pleth to remove unwanted components, identifying (606) a signal component of interest based on the filtered signal, monitoring (608) blood pressure changes, monitoring (610) heart rate, and performing (612) an analysis of the blood pressure signal to the heart rate signal to identify a phase relationship associated with the component of interest. Based on this phase relationship, the component of interest may be identified (614) as relating to the respiration or Mayer Wave. If it is related to the respiration wave (616), a respiratory parameter such as breathing rate may be determined (620). Otherwise, a Mayer Wave analysis (618) may be performed to obtain parameter information related to the autonomic nervous system.

39 Claims, 4 Drawing Sheets

U.S. PATENT DOCUMENTS

| | | | |
|---|---|---|---|
| 5,431,159 A | 7/1995 | Baker et al. | |
| 5,482,036 A | 1/1996 | Diab et al. | |
| 5,490,505 A | 2/1996 | Diab et al. | |
| 5,511,553 A | 4/1996 | Segalowitz | |
| 5,553,615 A | 9/1996 | Carim et al. | |
| 5,555,882 A | 9/1996 | Richardson et al. | |
| 5,575,284 A | 11/1996 | Athan et al. | |
| 5,623,933 A | 4/1997 | Amano et al. | |
| 5,755,229 A | 5/1998 | Amano et al. | |
| 5,766,127 A | 6/1998 | Pologe et al. | 600/310 |
| 5,776,071 A | 7/1998 | Inukai et al. | 600/493 |
| 5,813,989 A * | 9/1998 | Saitoh et al. | 600/484 |
| 5,830,137 A | 11/1998 | Scharf | 600/323 |
| 5,842,979 A | 12/1998 | Jarman | 600/322 |
| 5,853,364 A | 12/1998 | Baker, Jr. et al. | 600/300 |
| 5,862,805 A * | 1/1999 | Nitzan | 128/898 |
| 5,865,167 A | 2/1999 | Godik | |
| 5,865,756 A | 2/1999 | Peel, III | 600/490 |
| 5,885,213 A | 3/1999 | Richardson et al. | 600/336 |
| 5,902,235 A | 5/1999 | Lewis et al. | 600/323 |
| 5,919,134 A | 7/1999 | Diab | 600/323 |
| 5,931,779 A | 8/1999 | Arakaki et al. | 600/310 |
| 5,934,277 A | 8/1999 | Mortz | |
| 5,954,644 A | 9/1999 | Dettling et al. | 600/322 |
| 5,971,930 A | 10/1999 | Elghazzawi | 600/483 |
| 5,980,463 A | 11/1999 | Brockway et al. | 600/485 |
| 5,993,893 A | 11/1999 | Kikuchi | 427/8 |
| 5,997,482 A | 12/1999 | Vaschillo et al. | 600/484 |
| 6,011,985 A | 1/2000 | Athan et al. | 600/322 |
| 6,027,455 A | 2/2000 | Inukai et al. | 600/490 |
| 6,028,311 A | 2/2000 | Sodickson et al. | 250/343 |
| 6,064,910 A | 5/2000 | Andersson et al. | 607/20 |
| 6,067,462 A | 5/2000 | Diab et al. | 600/310 |
| 6,081,742 A | 6/2000 | Amano et al. | 600/513 |
| 6,099,481 A | 8/2000 | Daniels et al. | 600/538 |
| 6,129,675 A * | 10/2000 | Jay | 600/485 |
| 6,155,992 A | 12/2000 | Henning et al. | 600/583 |
| 6,236,872 B1 * | 5/2001 | Diab et al. | 600/323 |
| 6,358,201 B1 * | 3/2002 | Childre et al. | 600/300 |
| 6,480,733 B1 * | 11/2002 | Turcott | 600/516 |

* cited by examiner

A low frequency or substantially invariant component in relation to the time increments considered for blood oxygen saturation calculations, sometimes termed the "DC component," which generally corresponds to the attenuation related to the non-pulsatile volume of the perfused tissue and other matter that affects the transmitted plethysmographic signal. The second component, sometimes termed the "AC component," generally corresponds to the change in attenuation due to the pulsation of the blood. In general, the AC component represents a varying waveform which corresponds in frequency to that of the heartbeat. In contrast, the DC component is a more steady baseline component, since the effective volume of the tissue under investigation varies little or at a low frequency if the variations caused by the pulsation of the heart are excluded from consideration.

MONITORING PHYSIOLOGICAL PARAMETERS BASED ON VARIATIONS IN A PHOTOPLETHYSMOGRAPHIC BASELINE SIGNAL

FIELD OF THE INVENTION

The present invention relates, in general, to the noninvasive monitoring of physiological parameters such as respiration rate or low frequency heart rate/blood volume variability based on optical (visible and/or non-visible spectrum) signals and, in particular, to monitoring such parameters based on the processing of received optical signals to distinguish effects related to the patient's respiratory system and/or autonomic nervous system. The invention can be readily implemented in connection with pulse oximetry instruments so as to expand the utility of such instruments.

BACKGROUND OF THE INVENTION

Photoplethysmography relates to the use of optical signals transmitted through or reflected by a patient's blood, e.g., arterial blood or perfused tissue, for monitoring a physiological parameter of a patient. Such monitoring is possible because the optical signal is modulated by interaction with the patient's blood. That is, interaction with the patient's blood, generally involving a wavelength and/or time dependent attenuation due to absorption, reflection and/or diffusion, imparts characteristics to the transmitted signal that can be analyzed to yield information regarding the physiological parameter of interest. Such monitoring of patients is highly desirable because it is noninvasive, typically yields substantially instantaneous and accurate results, and utilizes minimal medical resources, thereby proving to be cost effective.

A common type of photoplethysmographic instrument is the pulse oximeter. Pulse oximeters determine an oxygen saturation level of a patient's blood, or related analyte values, based on transmission/absorption characteristics of light transmitted through or reflected from the patient's tissue. In particular, pulse oximeters generally include a probe for attaching to a patient's appendage such as a finger, earlobe or nasal septum. The probe is used to transmit pulsed optical signals of at least two wavelengths, typically red and infrared, through the patient's appendage. The transmitted signals are received by a detector that provides an analog electrical output signal representative of the received optical signals. By processing the electrical signal and analyzing signal values for each of the wavelengths at different portions of a patient's pulse cycle, information can be obtained regarding blood oxygen saturation.

The algorithms for determining blood oxygen saturation related values are normally implemented in a digital processing unit. Accordingly, one or more analog to digital (A/D) converters are generally interposed between the detector and the digital processing unit. Depending on the specific system architecture employed, a single multi-channel digital signal may be received by the digital processing unit or separate digital signals for each channel may be received. In the former case, the digital processing unit may be used to separate the received signal into separate channel components. Thus, in either case, the digital processing unit processes digital information representing each of the channels.

Such information defines input digital photoplethysmographic signals or digital "pleths." These pleths generally contain two components. The first component of interest is a low frequency or substantially invariant component in relation to the time increments considered for blood oxygen saturation calculations, sometimes termed the "DC component," which generally corresponds to the attenuation related to the non-pulsatile volume of the perfused tissue and other matter that affects the transmitted plethysmographic signal. The second component, sometimes termed the "AC component," generally corresponds to the change in attenuation due to the pulsation of the blood. In general, the AC component represents a varying waveform which corresponds in frequency to that of the heartbeat. In contrast, the DC component is a more steady baseline component, since the effective volume of the tissue under investigation varies little or at a low frequency if the variations caused by the pulsation of the heart are excluded from consideration.

Pulse oximeters typically provide as outputs blood oxygen saturation values and, sometimes, a heart rate and a graphical representation of a pulsatile waveform. The information for generating each of these outputs is generally obtained from the AC component of the pleth. In this regard, some pulse oximeters attempt to filter the DC component from the pleth, e.g., in order to provide a better digitized AC component waveform. Other pulse oximeters may measure and use the DC component, e.g., to normalize measured differential values obtained from the AC component or to provide measurements relevant to motion or other noise corrections. Generally, though, conventional pulse oximeters do not monitor variations in the DC component of a pleth or pleths to obtain physiological parameter information in addition to the outputs noted above.

SUMMARY OF THE INVENTION

The present invention is directed to using photoplethysmography to obtain physiological information related to respiration or the autonomic nervous system based on analysis of pleth characteristics separate from or in addition to the AC component or pulsatile waveform. The invention thus provides important diagnostic or monitoring information noninvasively. Moreover, various aspects of the invention can be implemented using one or more channels of a conventional pulse oximeter, thereby providing additional functionality to instruments that are widely available and trusted, as well as providing access to important information for treatment of patients on a cost-effective basis.

In a preferred implementation, the present invention obtains information regarding a physiological parameter based on analysis of the DC component of the pleth ("pleth baseline signal") to distinguish an effect related to the autonomic nervous system from an effect related to the respiratory system. It has been recognized that the pleth baseline signal can be analyzed to yield important information in this regard. In particular, it has been recognized that the pleth baseline signal includes at least three principal components: 1) a component related to respiration or the "respiration wave", 2) a low frequency component associated with the autonomic nervous system or vaso motor center, sometimes termed the "Mayer Wave", and 3) a very low frequency component which is associated with temperature control. Regarding the second of these, the origin and nature of the Mayer Wave is not fully settled. For present purposes, the Mayer Wave relates to a low frequency variation in blood pressure, heart rate, and/or vaso constriction.

The first two components noted above have particular significance for diagnostic and patient monitoring purposes. In particular, the amplitude and frequency of the Mayer Wave are seen to change in connection with hypertension, sudden cardiac death, ventricular tachycardia, coronary artery disease, myocardial infarction, heart failure, diabetes, and autonomic neuropathy and after heart transplantation. Respiration rate is monitored during a variety of medical procedures, for example, as an indication of a patient's stress levels and to identify patient respiratory distress. The present invention is based, in part, on the recognition that effects related to these components can be monitored based on analyzing a pleth to identify physiological parameter information. In particular, it is expected that both the Mayer and respiration waves influence heart rate (and related parameters such as variations in blood pressure and blood volume) by direct influence on the vaso motor center. In the latter case, this is by a "spillover" from the breathing center to the vaso motor center, which increases heart rate during inspiration.

A difficulty associated with obtaining physiological parameter information based on the Mayer Wave and the respiration wave relates to distinguishing the effects associated with these waves, particularly in view of the fact that each of these waves can occur within overlapping frequency ranges. In accordance with the present invention, physiological parameter information is obtained by distinguishing these two pleth components in any of various ways. These generally include distinguishing the waves based on frequency, based on a wave characteristic other than frequency and based on information not directly derived from Mayer/respiration wave comparison. With regard to distinguishing the waves based on frequency, as noted above, the Mayer Wave and respiration wave may occur in overlapping frequency bands. Accordingly, a process for distinguishing those waves based on frequency may be assisted by modifying one or both of these wave frequencies to create a cognizable basis of distinction. In some cases, this can be accomplished by controlling or having the patient control his respiration rate.

Alternatively, the waves may be distinguished based on a wave characteristic other than frequency such as waveform or phase. In the latter regard, it has been recognized that the respiration and Mayer waves may influence blood pressure by a change in heart rate and vasoconstriction. Respiration, however, causes a change in blood pressure because of thoracic pressure differences during inspiration and expiration. Inspiration causes a decrease in left ventricular filling, decreasing the blood pressure. Accordingly, during inspiration blood pressure drops and heart rate rises. In contrast, in the rising part of the Mayer Wave, both blood pressure and heart rate are increased simultaneously. Therefore, blood pressure and heart rate changes will be out of phase if they are caused by respiration, while in a Mayer Wave they are in phase.

The Mayer and respiration waves may also be distinguished based on information not directly derived from Mayer/respiration wave comparison. For example, increases in blood oxygen levels over a predetermined frequency range may be correlated with known physiological effects caused by respiration. More particularly, increases in the ratio of oxygenated hemoglobin over deoxygenated hemoglobin over a frequency of 0 to 0.5 Hz (or frequencies of 1 Hz or greater in the case of neonates) may be caused due to inspiration, which has the effect of lowering the amount of venous blood in the tissue and thus increases the ratio of arterial blood to venous blood in the tissue. Such effects may be indicated, for example, by monitoring pleths associated with multiple channels to identify variations in blood oxygenation within the relevant frequency bands. It will be appreciated that this allows for distinguishing an effect associated with the respiration wave without directly separating or otherwise comparing a respiration wave component and a Mayer Wave component.

Once an effect is associated with one of the respiration wave and the Mayer Wave has been distinguished, this can be used to obtain physiological parameter information. Depending on the specific implementation, as discussed above, the waves may be distinguished based on a known characteristic of one of the waves, a known difference between the waves, or a secondary effect associated with one of the waves. In cases where the waves are distinguished based on a known characteristic or secondary effect of one of the waves, the physiological parameter information may be derived from the wave having the known characteristic or secondary effect, from the other wave, or from a signal including both wave components.

In accordance with one aspect of the present invention, a method is provided for monitoring a physiological parameter of a patient. The method includes the steps of obtaining a pleth that includes at least a first component associated with the operation of the patient's respiratory system and a second component associated with the patient's autonomic nervous system, processing the pleth to distinguish an effect associated with one of the first and second components from an effect associated with the other of the components, and using this distinguished effect to monitor the physiological parameter. Depending on the specific implementation, this step of obtaining a pleth may involve obtaining information corresponding to a single channel of transmitted light (visible and/or nonvisible spectrum) or multiple channels. For example, the invention may be implemented in connection with a conventional pulse oximeter that provides at least two separate channels and corresponding pleths. One or both of these pleths may be utilized in monitoring the physiological parameter of interest. The step of processing the pleth may involve distinguishing a Mayer Wave effect from a respiration wave effect, for example, in any of the ways discussed above. The physiological parameter monitored may be a respiratory parameter such as respiration rate or a Mayer Wave parameter such as low frequency heart rate variations or blood volume variations. An associated apparatus includes a port for receiving the pleth and a processor operative for processing the pleth signal to distinguish effects associated with the first and second components. A system incorporating such an apparatus may include one or more transmitters for transmitting an optical signal, and a detector signal for detecting the transmitted optical signals and providing the pleth based thereon.

In accordance with another aspect of the present invention, a method is provided for monitoring a patient's breathing. The method involves the steps of transmitting an optical signal relative to a patient such that the signal interacts with perfused tissue of the patient, operating a detector system to detect the transmitted optical signal and provide a pleth reflective of the detected optical signal, where the pleth includes at least a first component associated with the patient's respiratory system and a second component associated with the patient's autonomic nervous system, processing the pleths to distinguish an effect associated with the first component from effects associated with the second component and using the distinguished effect to monitor the patient's breathing. In one implementation, a respiratory effect is distinguished from an autonomic nervous system effect based on a phase difference between the associated waves. In particular, blood pressure and heart rate changes will have one phase relationship if they are caused by respiration and another phase relationship if they are associated with a Mayer Wave. Thus, by acquiring both the changes in blood pressure and heart rate, the phase relationship can be determined to distinguish effects associated with the respiration wave from effects associated with the Mayer Wave. This information is then used to identify pleth characteristics associated with respiration which are, in turn, monitored to determine the respiration rate.

The present invention thus allows pleths to be analyzed to monitor physiological parameters related to operation of the respiration system and/or the autonomic nervous system. Such parameters can be monitored noninvasively based on one or more channels of optical signals transmitted relative to a patient. The invention can be implemented in connection with conventional pulse oximetry components so as to expand the functionality of such instruments as well as to provide important physiological parameter information in a cost effective manner.

BRIEF DESCRIPTION OF THE DRAWINGS

For a more complete understanding of the present invention and further advantages thereof, reference is now made to the following detailed description, taken in conjunction with the drawings, in which.

DETAILED DESCRIPTION

The present invention relates to obtaining physiological parameter information for a patient based on an analysis of a pleth signal involving distinguishing an effect associated with a Mayer Wave component from an effect associated with a respiration wave component. In the following discussion, the invention is described in the context of an implementation utilizing components of a conventional pulse oximeter. The invention has particular advantages in this regard as such an implementation enhances the functionality of conventional pulse oximeters and provides important physiological parameter information in a cost effective manner. However, it will be appreciated that various aspects of the invention are not limited to such a pulse oximeter or other multi-channel signal implementation and the invention may be embodied in a dedicated single or multi-channel photoplethysmography instrument. Moreover, although the discussion below is primarily directed to monitoring respiration based on distinguishing a respiration wave effect from a Mayer Wave effect, it will be appreciated that a variety of parameters may be monitored once these effects are distinguished. Accordingly, the following discussion should be understood as exemplifying the invention and not by way of limitation.

Figure 1:
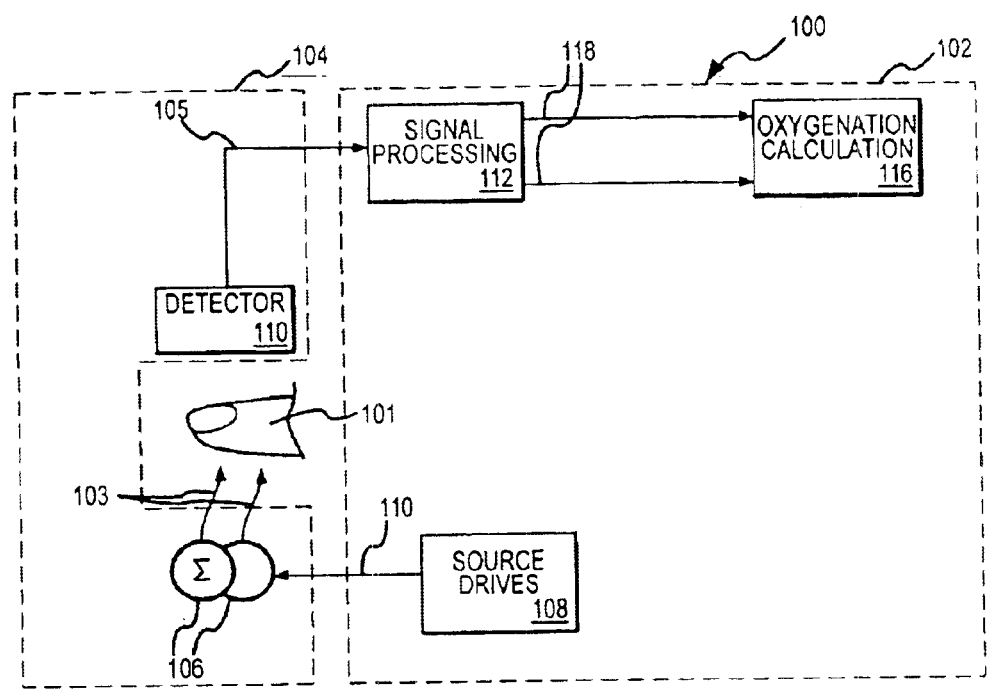
FIG. 1 is a schematic diagram of a pulse oximeter in accordance with the present invention.

Referring to FIG. 1, a schematic diagram of a pulse oximeter 100 in accordance with the present invention is shown. The oximeter 100 generally includes an instrument housing 102 and a probe 104 for attachment to a finger 101 or other appendage of a patient under analysis. In the illustrated embodiment, the probe 104 includes two or more sources 106 and a detector 110. It will be appreciated that either or both of these components may alternatively be located in the housing 102 and may be optically connected to the probe 104 by fiber optics or the like. Additionally, the sources 106 and/or detector 110 may be located in the cable or other coupling operatively between the probe 104 and the housing 102. The sources 106 are driven by source drives 108. The drives 108 serve to modulate the signals 103 in any of various ways. In this regard, the signals 103 transmitted by the sources 106 may be time division multiplexed, frequency division multiplexed, code division multiplexed, or the like. Such multiplexing facilitates separation of the signals from each of the channels during hardware or software based signal processing. The sources 106 provide two or more channels of signals 103. Each channel has a unique spectral content, e.g., wavelength or wavelength band. In the illustrated embodiment, two sources 106 are shown; one of the sources may have a red-centered wavelength and the other may have an infrared-centered wavelength.

The signals 103 may be transmitted through or reflected by the patient's tissue. In either case, the signals are modulated by the patient's tissue to provide information regarding blood oxygen saturation in a manner that is well known. The transmitted signals 103 are received by the detector 110 which, in the illustrated embodiment, provides an analog current output signal 105 representative of the detected signals 103. This detector signal 105 is then processed by signal processing module 112. The processing module 112 may include a number of components that may be embodied in software, firmware and/or hardware. These components may include components for amplifying the signal 105 and converting the signal from a current signal to a voltage signal, filtering the signal to remove certain components of noise and otherwise conditioning the signal. In the illustrated embodiment, the signal processing module 112 also includes an analog to digital converter for converting the signal into a digital signal and a demultiplexer component for providing two separate output signals 118 or pleths that generally correspond to the two separate channel signals 103. These pleths 118 are then used by oxygenation calculation module 116 to compute a value related to blood oxygen saturation, e.g., a blood oxygen saturation percentage. A number of algorithms for performing such calculations are known and such calculation techniques are disclosed in U.S. Pat. Nos. 5,934,277 by Mortz and 5,842,979 by Jarman, both of which are incorporated herein by reference.

Figure 2:
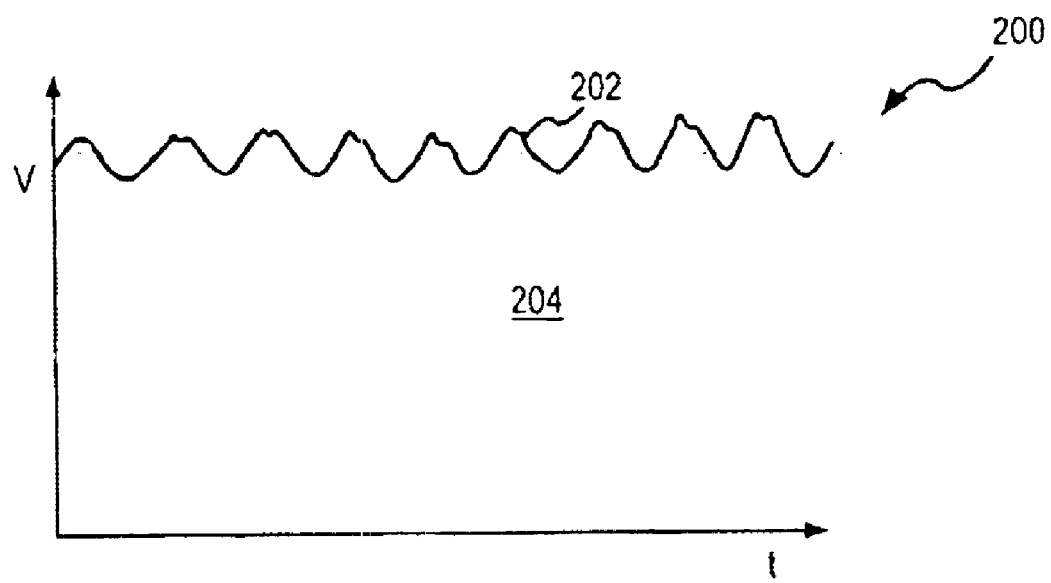
FIG. 2 illustrates the waveform of a pleth that may be used to obtain physiological parameter information in accordance with the present invention.

FIG. 2 generally illustrates a pleth waveform corresponding to one of the optical channels. As shown, the waveform 200 generally includes a pulsatile component 202 having a relatively small magnitude carried by a baseline component 204 of larger magnitude. The pulsatile component 202 is the component that is primarily used in pulse oximetry to determine blood oxygenation. This component or the overall signal 200 may also be used in accordance with the present invention, for example, to monitor pulse rate. The baseline component 204, sometimes termed the "DC component," includes lower frequency components that reflect important physiological information that may be monitored in accordance with the present invention. In particular, it has been recognized that the baseline component includes a number of sub-components including a Mayer Wave component, a respiration wave component, and other components such as a very low frequency component which is associated with temperature control The effects related to the respiration wave and the Mayer Wave have particular significance in relation to the implementations of the present invention described below.

Respiration is believed to have a number of effects on circulation that may be reflected in a pleth. First, the respiratory center in the brain directly influences the vasomotor center, causing respiratory sinus arrhythmia associated with increased heart rate during inspiration and decreased heart rate during expiration. Additionally, the thoracic pressure decreases upon inspiration, increasing the blood content in the chest causing: 1) decreased blood return to the left ventricle, 2) increased blood return to the right ventricle, and 3) decreased venous pressure. Respiration is also believed to produce a rise in arterial pressure during the early part of expiration and a fall in pressure during the remainder of the respiratory cycle. Thus, the prominent effect on arterial pressure is apparently item 1) above. During deep respiration, the blood pressure can rise and fall by as much as 20 mm hg. It has also been recognized in relation to the present invention that the effect of respiration on venous blood outside the thorax is a decrease during inspiration and an increase in venous filling and pressure during expiration.

As noted above, the Mayer Wave is not fully understood. However, the Mayer Wave is believed to relate to an oscillation of the pressure reflex control system attributed mainly to the baroreceptor reflex. The associated cycle is as follows: 1) the baroreceptors sense an increase in pressure and inhibit the sympathetic system which reduces the pressure, 2) this pressure drop causes the baroreceptors to excite the sympathetic nerve system and the blood pressure rises and the cycle starts over. The response of the pressure to the reflex is not instantaneous; it may take a few seconds. The period of the Mayer Wave is generally taken to be between about 6–20 seconds in humans or around 0.05–0.15 Hz. The duration is different in other subjects. The amplitude of the wave can be as high as 40 mm hg, but varies between individuals, decreases with age and increases upon concentration.

In accordance with the present invention, physiological parameter information is obtained based on distinguishing an effect associated with the Mayer Wave from an effect associated with the respiration wave. Once such effects are distinguished, the Mayer Wave, the respiration wave or both can be analyzed to obtain the desired information, e.g., regarding the respiratory system, the automatic nervous system or related diagnostics.

The Mayer Wave and the respiration wave can be distinguished in a variety of ways, as noted above. These include based on frequency, based on a wave characteristic other than frequency and based on information not directly derived from Mayer/respiration wave comparison. With regard to the first of these, distinguishing the waves based on frequency, this can be accomplished in some cases by controlling or having the patient control his respiration rate. An associated methodology and processing system that thereby isolates and analyzes Mayer Wave effects is described in U.S. patent application Ser. No. [not yet assigned] entitled "Monitoring Mayer Wave Effects Based on a Photoplethysmographic Signal," filed concurrently herewith. With regard to the last of the categories noted above, distinguishing the waves based on information not directly derived from Mayer Wave/respiration wave comparison, this can be accomplished by a multi-channel, blood analyte analysis to identify effects related to variations in the ratio of arterial and venous blood in the tissue under consideration associated with the respiratory cycle. An associated methodology and processing system that thereby isolates and analyzes respiration wave effects is described in U.S. patent application Ser. No. [not yet assigned] entitled "Apparatus and Method for Monitoring Respiration with a Pulse Oximeter," filed concurrently herewith.

Figure 3:
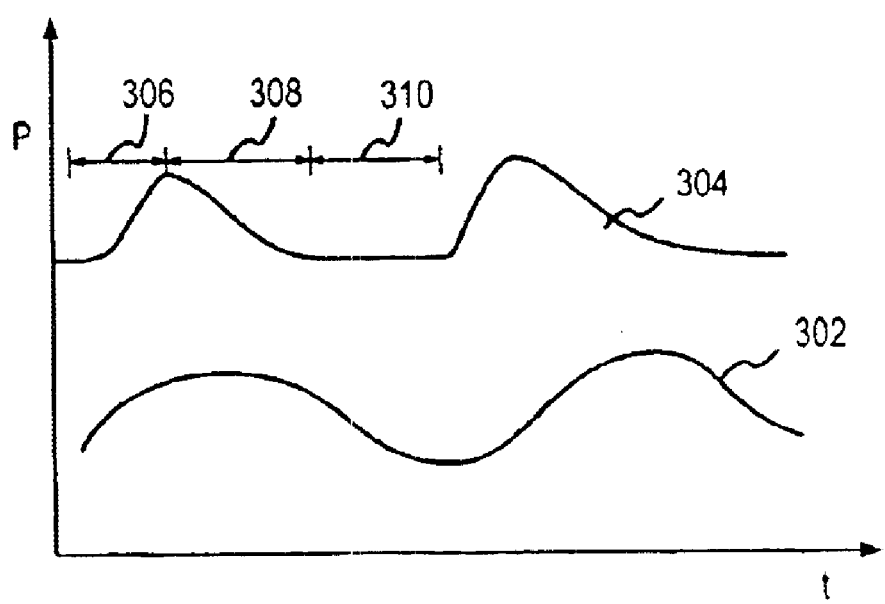
FIG. 3 is a graph illustrating the waveforms of a Mayer Wave and a respiration wave.

The following description concerns the remaining category noted above, distinguishing the waves based on a wave characteristic other than frequency. Although any characteristic that yields a cognizable distinction in this regard may be utilized, two apt characteristics are waveform and phase. FIG. 3 illustrates a difference in waveform that may be used to distinguish Mayer Wave effects from respiration wave effects. In particular, FIG. 3 generally illustrates the waveform of a Mayer Wave 302 and of a respiration wave 304. As shown, the Mayer Wave 302 is generally expected to have a simple sinusoidal shape with similar rise times and fall times. The respiration wave 304 is not. In general, the time period associated with inspiration 306 is shorter than that of expiration 308. In addition, there is a significant rest time 310 during the respiration cycle, especially at low breathing rates. The associated waveform, as reflected in a measured parameter (generally denoted p) such as changes in heart rate or blood pressure, therefore differs from the Mayer waveform as generally shown in FIG. 3. Thus, the Mayer Wave and respiration wave effects can be distinguished by identifying a component of interest in the pleth, monitoring the waveforms of the Mayer Wave and respiration wave using an appropriate measurement parameter, and correlating one of the waveforms to the pleth component of interest.

In this regard, the patient's heart rate and/or blood pressure can be monitored photoplethysmographically or in any other suitable manner. Appropriate methodologies for monitoring measured parameters such as heart rate photoplethysmographically are disclosed in the above-noted applications filed concurrently herewith. Thus, in accordance with the present invention, a filter such as a band pass filter can be used to extract a component wave from the pleth, the waveform of the extracted wave can be compared to, e.g., a heart rate waveform to verify that the extracted component wave is a Mayer Wave or a respiration wave, and the extracted component wave can then be analyzed to obtain physiological parameter information. For example, where the extracted component wave is a Mayer Wave, it can be monitored to identify changes of frequency and amplitude that may have diagnostic significance. Where the extracted component wave is a respiration wave, its frequency can be monitored to track respiration rate.

Figure 4:
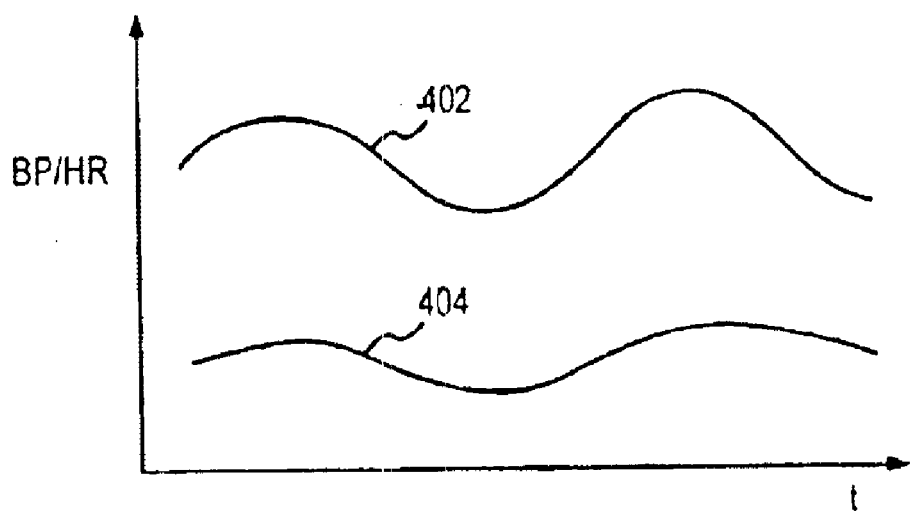
FIG. 4 is a chart illustrating a phase relationship between a blood pressure signal and a heart rate signal corresponding to a Mayer Wave component of a pleth.
Figure 5:
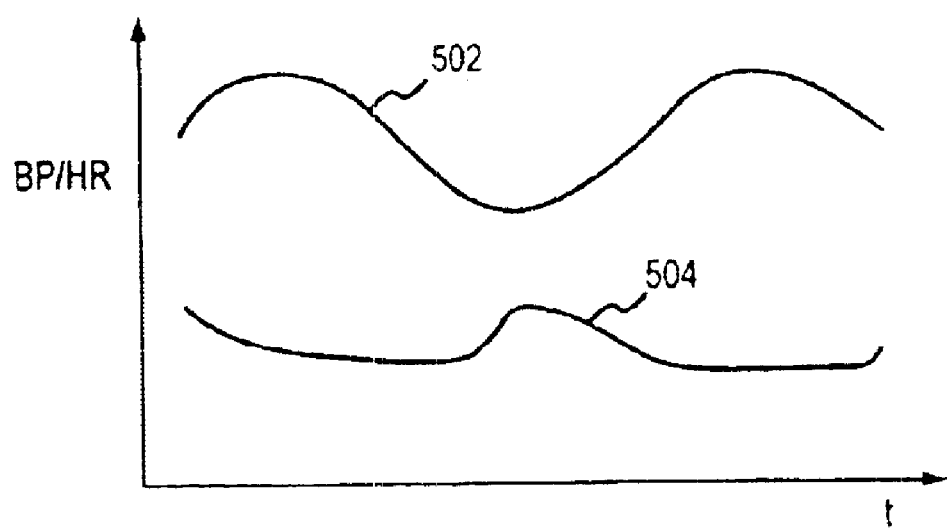
FIG. 5 is a chart illustrating a phase relationship between a blood pressure signal and a heart rate signal for a respiration wave component of a pleth.

The Mayer Wave and respiration wave can also be distinguished based on differing phase relationships of associated parameters. This is illustrated in FIGS. 4 and 5. In particular, FIG. 4 shows the plot of blood pressure 402 and heart rate 404 versus time associated with the Mayer Wave. As shown, the Mayer Wave influences blood pressure by a change in heart rate and vaso constriction. In the rising part of the Mayer Wave, both blood pressure and heart rate are increased simultaneously. Thus, the illustrated waves are substantially in phase.

In contrast, FIG. 5 shows the waveforms associated with a respiration wave. Respiration causes a change in blood pressure (as indicated by waveform 502) because of thoracic pressure differences during inspiration and expiration. Inspiration causes a decrease in left ventricular filling, decreasing the blood pressure (as indicated by waveform 504). Thus, the illustrated waveforms 502 and 504 are out of phase. Accordingly, blood pressure and heart rate changes will generally be out of phase if they are caused by respiration and in phase if they are caused by a Mayer Wave. By acquiring both the changes in blood pressure and heart rate, one can determine the existence of a phase difference, making it possible to distinguish between the respiration and Mayer Wave. Both can be acquired using a pulse oximeter in the following manner:

1. The blood pressure changes can be monitored by acquiring the pleth, which is related to the amount of blood present in the finger, which is directly proportional to the blood pressure. Acquiring the pleth and filtering out unwanted components such as the very low frequencies and the heart rate will give the variation in blood volume, and thus pressure, of the Mayer and respiration waves. The signals corresponding to one or more channels of the pulse oximeter can be used in this regard.

2. The changes in heart rate can be determined by detecting the pulses in the unfiltered plethysmographic signal and determining the time between them. The heart rate will change due to respiration and the Mayer Wave. Thus, an effect of interest can be identified based on appropriate processing, e.g., mathematical or spectral analysis of the pleth. Once this effect or component of interest is identified, corresponding heart rate and blood pressure waveforms can be obtained as described above. Analysis of these waveforms with regard to the phase relationships therebetween yields information as to whether the effect under analysis is associated with the Mayer Wave or the respiration wave. It will be appreciated that, although this process has been illustrated graphically to facilitate a better understanding, the associated methodology can be readily implemented in software or other processing components. Finally, once an effect is thereby distinguished, it can be used to obtain physiological parameter information. For example, as noted above, the respiration wave reflects the respiratory cycle. Once the pleth baseline signal is resolved into its Mayer Wave and respiration wave components, the respiration wave component can be analyzed to obtain respiration rate, e.g., based on identification of successive waveform peaks to obtain the period of respiration or based on spectral analysis/filtering (e.g., involving a Fast Fourier Transform to obtain the fundamental frequency of respiration wave).

Figure 6:
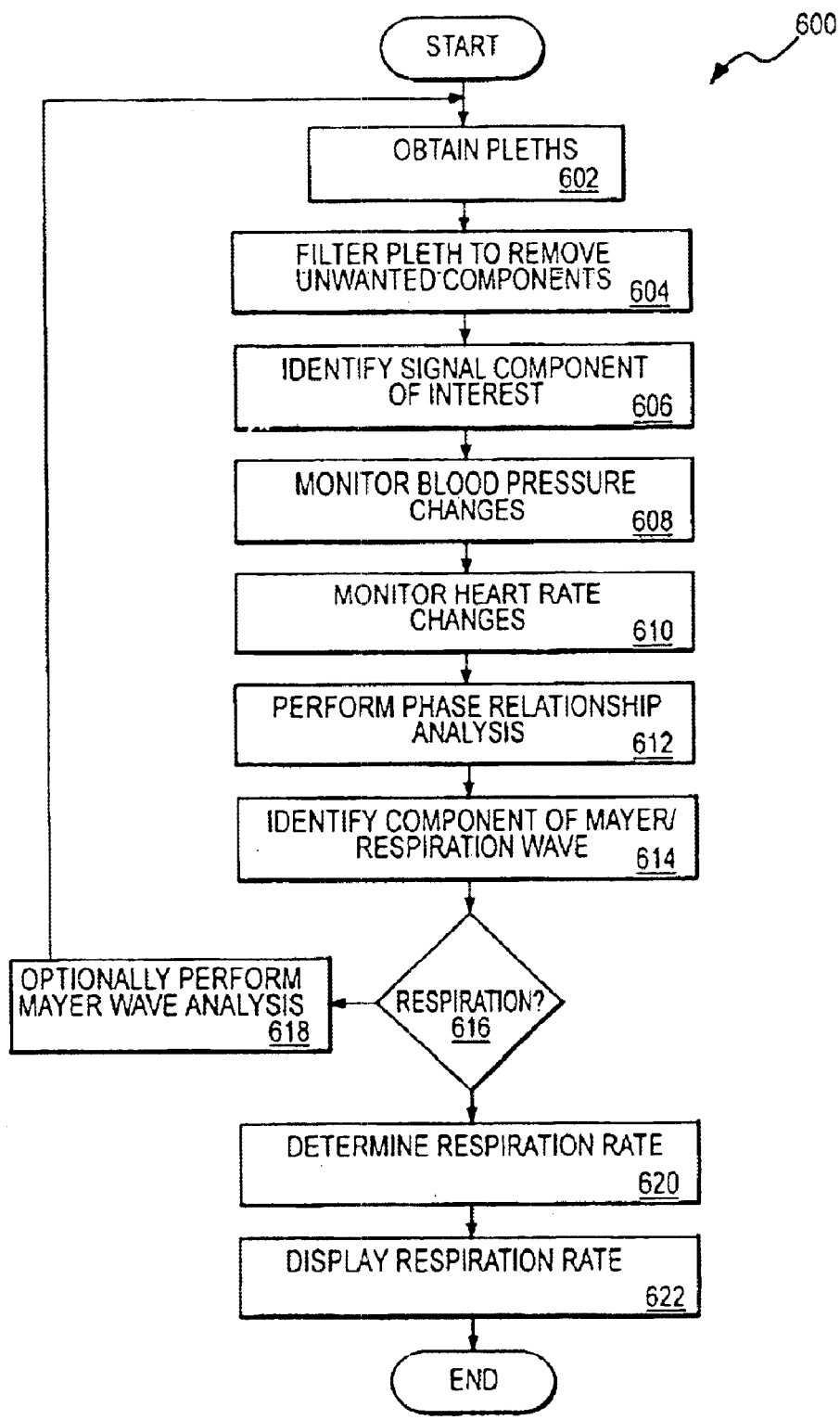
FIG. 6 is a flow chart illustrating a process for obtaining physiological parameter information based on distinguishing an effect associated with a Mayer Wave from an effect associated with a respiration wave in accordance with the present invention.

The associated process 600 may be summarized by reference to the flow chart of FIG. 6. The process 600 is initiated by obtaining (602) one or more pleths for analysis. The present invention may be implemented in connection with a conventional pulse oximeter. In this regard, a pleth corresponding to one of the red and infrared channels, e.g., whichever signal appears to have a better signal to noise ratio, or a composite signal may be utilized. This pleth may then be filtered (604) to remove unwanted components. For example, the pulsatile component may be separated from the pleth baseline component by one or more band pass filters, high pass filters, low pass filters, or other hardware or software components. In this regard, it is noted that the pulsatile component will generally have a higher frequency that can be readily distinguished from the pleth baseline component including the Mayer Wave and respiration wave.

Once the pleth has been filtered, an effect of interest may be identified (606) based on analysis of the filtered pleth baseline component. For example, a mathematical or spectral analysis may be used to resolve the pleth baseline signal into two primary components. Then, blood pressure changes may be monitored (608) relative to the identified effect using the filtered pleth (pleth baseline component). Heart rate may be monitored (610) using the unfiltered pleth or the pulsatile component. Using the resulting blood pressure and heart rate signals, an analysis is performed (612) to identify a phase relationship associated with the pleth component of interest. The pleth component of interest is thereby identified (614) as relating to the respiration wave or the Mayer Wave based on the phase relationship. If the component is identified as being associated with the respiration wave (616), then the respiration rate may be determined (620) based on a period measurement or primary frequency analysis. In this regard, the frequency band of interest will generally be 0–0.5 Hz for adult 5 patients but may be extended, e.g., to 0–1.5 Hz for newborns. The resulting respiration rate may then be output (622) on a display of the pulse oximeter and/or in hard copy form, e.g., on tape. If the identified component is not associated with the respiration wave, then a Mayer Wave analysis may optionally be performed (618), for example, to monitor a parameter related to the autonomic nervous system and additional pleth signals may be analyzed to identify a respiration wave effect if desired.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed:

1. A method for use in noninvasively monitoring a physiological parameter of a patient, comprising the steps of:
   obtaining a photoplethysmographic ("pleth") signal that is modulated based on interaction of a transmitted optical signal with blood of said patient, wherein said pleth signal includes at least a first respiratory component and a second Mayer wave component associated with the patient's autonomic nervous system;
   processing said pleth signal relative to said first and second components to distinguish effects associated with said first respiratory component from effects associated with said second Mayer wave component; and
   monitoring a respiration rate of said patient's breathing using at least one said distinguished effect.

2. A method as set forth in claim 1, wherein said first component relates to the patient's respiratory sinus arrhythmia.

3. A method as set forth in claim 1, further comprising determining first information related to a first signal defined by variations in blood pressure over time, determining second information related to a second signal defined by variations in heart rate over time, and using said first information and said second information to obtain third information related to a phase difference between said first signal and said second signal.

4. A method as set forth in claim 3, wherein said substep of distinguishing further comprises using said identified phase difference to analyze said pleth signal so as to obtain information related to said first component.

5. A method as set forth in claim 1, wherein said step of obtaining comprises the substeps of:
   providing at least one source for transmitting an optical signal;
   operating said at least one source to transmit said optical signal relative to said patient such that said signal interacts with said blood of said patient;
   providing a detector system and generating said detector system to detect said transmitted optical signal and provide said pleth signal reflective of said detected optical signal; and providing a processor and operating said processor to obtain said pleth signal.

6. A method as set forth in claim 5, wherein said substep of providing at least one source comprises providing two sources having different spectral contents.

7. A method as set forth in claim 1, further comprising using said pleth signal to monitor information related to both blood pressure and heart rate.

8. A method as set forth in claim 7, wherein said monitoring information related to blood pressure step comprises acquiring at least a portion of the pleth signal, filtering at least one component from the acquired signal portion, and determining information regarding a variation in blood volume over time related to the first and second components.

9. A method as set forth in claim 7, wherein said monitoring information related to heart rate step comprises acquiring at least a pulsatile portion of the pleth signal and determining information regarding a variation in heart rate over time related to the first and second components.

10. A method as set forth in claim 1, further comprising determining first information related to a first signal defined by variations in blood pressure over time, determining second information related to a second signal defined by variations in heart rate over time, and using said first information and said second information to obtain third information related to a difference in waveform between said first signal and said second signal.

11. A method for use in monitoring a patient's breathing comprising the steps of:
transmitting an optical signal relative to said patient such that said signal interacts with blood of said patient;
operating a detector system to detect said transmitted optical signal and provide a photoplethysmographic ("pleth") signal reflective of said detected optical signal, where said pleth signal includes at least a first respiratory component and a second Mayer wave component associated with the patient's autonomic nervous system;
first processing said pleth signal to isolate a pulsatile pleth signal and a baseline pleth signal;
second processing said baseline pleth signal to distinguish effects associated with the said first respiratory component from effects associated with said second Mayer wave component; and
using said distinguished effects to monitor said patient's breathing.

12. A method as set forth in claim 11, wherein said step of distinguishing comprises determining first information related to a first signal defined by variations in blood pressure over time, determining second information related to a second signal defined by variations in heart rate over time, and using said first information and said second information to obtain third information related to a phase difference between said first signal and said second signal.

13. A method as set forth in claim 12, wherein said step of distinguishing further comprises using said identified phase difference to analyze said pleth signal so as to obtain information related to said first component.

14. A method as set forth in claim 11, wherein said substep of distinguishing comprises determining first information related to a first signal defined by variations in blood pressure over time, determining second information related to a second signal defined by variations in heart rate over time, and using said first information and said second information to obtain third information related to a difference in waveform between said first signal and said second signal.

15. A method as set forth in claim 11, wherein said first component relates to the patient's respiratory sinus arrhythmia.

16. A method as set forth in claim 11, wherein said substep of monitoring comprises measuring said patient's respiration rate.

17. A method as set forth in claim 11, wherein said step of transmitting comprises operating one or more sources to provide a first channel of said signal having a first spectral content and a second channel of said optical signal having a second spectral content different from said first spectral content.

18. A method as set forth in claim 11, wherein said step of distinguishing comprises using said baseline signal to monitor information related to one of blood pressure and heart rate.

19. A method as set forth in claim 18, wherein said monitoring information related to blood pressure step comprises acquiring at least a portion of the baseline signal, filtering at least one component from the acquired signal portion and determining information regarding a variation in blood volume over time related to the first and second components.

20. A method as set forth in claim 18, wherein said monitoring information related to heart rate step further comprises acquiring at least a pulsatile portion of the pleth signal and determining information regarding a variation in heart rate over time related to the first and second components.

21. An apparatus for use in monitoring a patient's breathing, comprising:
a port for receiving a photoplethysmographic ("pleth") signal that is modulated based on interaction of a transmitted optical signal with blood of said patient, wherein said pleth signal includes at least a first component associated with the operation of the patient's respiratory system and a second component associated with the patient's autonomic nervous system; and
a processor operated for processing the pleth signal to distinguish an effect associated with one of said first and second components from an effect associated with the other of said components, wherein said processor is operative for distinguishing said effect by determining first information related to a first signal defined by variations in blood pressure over time, determining second information related to a second signal defined by variations in heart rate over time, and using said first information and said second information to obtain third information related to a waveform difference between said first signal and said second signal and for using said distinguished effect to monitor said physiological parameter.

22. An apparatus as set forth in claim 21, wherein said processor is operative for measuring said patient's respiration rate and providing an output indicative thereof.

23. An apparatus as set forth in claim 21, wherein said processor is operative to determine a phase difference between a waveform associated with said first signal and a waveform associated with said second signal.

24. An apparatus as set forth in claim 21, wherein said processor is operative for using said identified phase difference to analyze said pleth signal so as to obtain information related to said first component.

25. An apparatus as set forth in claim 21, wherein said heart rate is monitored by acquiring at least a pulsatile pleth signal and determining information regarding a variation in heart rate over time related to the first and second components.

26. An apparatus as set forth in claim 21, further comprising at least one source for transmitting an optical signal relative to said patient such that said signal interacts with said blood of said patient; and
 a detector system for detecting said transmittal optical signal and providing said pleth signal such that said pleth signal is reflective of said detective optical signal.

27. An apparatus as set forth in claim 26, wherein said detector system comprises a sensor for receiving the transmitted optical signal and providing a sensor output reflective of said received optical signal and circuitry for processing said sensor output signal to provide said pleth signal.

28. An apparatus as set forth in claim 26, wherein said at least one source is operative to provide a first channel of said optical signal having a first spectral content and a second channel of said optical signal having a second spectral content different from laid first spectral content.

29. An apparatus as set forth in claim 21, wherein the processor is operative for distinguishing an effect associated with said first component and using said effect to monitor said patient's breathing.

30. An apparatus as set forth in claim 21, wherein said blood pressure is monitored by acquiring at least a portion of the pleth signal, filtering at least one component from the acquired signal portion, and determining information regarding a variation in blood volume over time related to the first and second components.

31. A method for use in noninvasively monitoring a physiological parameter of a patient, comprising the steps of:
 obtaining a photoplethysmographic ("pleth") signal that is modulated based on interaction of a transmitted optical signal with blood of said patient, wherein said pleth signal includes at least a first component associated with the operation of the patient's respiratory system and a second component associated with the patient's autonomic nervous system;
 processing said pleth signal relative to said first and second components;
 distinguishing an effect associated with one of said first and second components from an effect associated with the other of said components, wherein said distinguishing comprises determining first information related to a first signal defined by variations in blood pressure over time, determining second information related to a second signal defined by variations in heart rate over time, and using said first information and said second information to obtain third information related to a waveform difference between said first signal and said second signal; and
 using said distinguished effect to monitor said physiological parameter.

32. A method as set forth in claim 31, wherein said step of distinguishing comprises distinguishing an effect associated with said first component and said step of using comprises the step of monitoring said patient's breathing.

33. A method as set forth in claim 31, wherein monitoring said heart rate comprises acquiring at least a pulsatile portion of the pleth signal and determining information regarding a variation in heart rate over time related to the first and second components.

34. A method as set forth in claim 31, wherein monitoring said heart rate comprises acquiring at least a baseline portion of the pleth signal and determining information regarding a variation in heart rate over time related to the first and second components.

35. A method as set forth in claim 31, wherein monitoring comprises measuring said patient's respiration rate.

36. A method as set forth in claim 31, wherein said waveform difference between said first signal and said second signal comprises a phase difference.

37. A method as set forth in claim 36, wherein said step of distinguishing further comprises using said identified phase difference to analyze said pleth signal so as to obtain information related to said first component.

38. A method as set forth in claim 31, wherein said first component relates to the patient's respiratory sinus arrhythmia.

39. A method as set forth in claim 31, wherein said second component relates to a Mayer Wave of said patient.

* * * * *

UNITED STATES PATENT AND TRADEMARK OFFICE
CERTIFICATE OF CORRECTION

PATENT NO. : 6,896,661 B2
DATED : May 24, 2005
INVENTOR(S) : Dekker

It is certified that error appears in the above-identified patent and that said Letters Patent is hereby corrected as shown below:

Column 13,
Line 8, delete "transmittal", and insert therefor -- transmitted --;
Line 10, delete "detective", and insert therefor -- detected --; and
Line 20, delete "laid", and insert therefor -- said --.

Signed and Sealed this

Sixteenth Day of August, 2005

JON W. DUDAS
*Director of the United States Patent and Trademark Office*